United States Patent
Patel et al.

(10) Patent No.: US 10,098,868 B2
(45) Date of Patent: *Oct. 16, 2018

(54) FORMULA COMPRISING A HYPOLIPIDEMIC AGENT

(71) Applicant: Cadila Healthcare Limited, Ahmedabad, Gujarat (IN)

(72) Inventors: Jitendre D. Patel, Ahmedabad (IN); Prakash Davadra, Gujarat (IN); Snehal Patel, Gujarat (IN); Shafiq Sheikh, Gujarat (IN)

(73) Assignee: Cadila Healthcare Limited, Ahmedabad (IN)

(*) Notice: Subject to any disclaimer, the term of this patent is extended or adjusted under 35 U.S.C. 154(b) by 0 days.

This patent is subject to a terminal disclaimer.

(21) Appl. No.: 15/475,812

(22) Filed: Mar. 31, 2017

(65) Prior Publication Data

US 2017/0266158 A1    Sep. 21, 2017

Related U.S. Application Data

(63) Continuation of application No. 14/899,912, filed as application No. PCT/IN2014/000489 on Jul. 24, 2014, now Pat. No. 9,610,277.

(30) Foreign Application Priority Data

Jul. 25, 2013 (IN) .......... 2470/MUM/2013

(51) Int. Cl.
*A61K 31/40*    (2006.01)
*A61K 9/20*    (2006.01)

(52) U.S. Cl.
CPC ............ *A61K 31/40* (2013.01); *A61K 9/2009* (2013.01); *A61K 9/2013* (2013.01)

(58) Field of Classification Search
CPC ..... A61K 31/40; A61K 9/2009; A61K 9/2013
See application file for complete search history.

(56) References Cited

U.S. PATENT DOCUMENTS

| 4,231,938 A | 11/1980 | Monaghan et al. |
| 4,346,227 A | 8/1982 | Terahara et al. |
| 4,444,784 A | 4/1984 | Hoffman et al. |

(Continued)

FOREIGN PATENT DOCUMENTS

| EP | 1586571 A1 | 10/2005 |
| IN | 1910/MUM/2013 | 12/2014 |

(Continued)

OTHER PUBLICATIONS

Ansel et al. "Pharmaceutical Dosage Forms and Drug Delivery Systems, Seventh Edition" 1999, pp. 88-92.

(Continued)

*Primary Examiner* — Savitha M Rao
(74) *Attorney, Agent, or Firm* — Goodwin Procter LLP

(57) ABSTRACT

The present invention relates to the stable pharmaceutical composition of a suitable hypolipidemic agent. Preferably, the present invention discloses novel formulations of the compound of formula (I), or pharmaceutically acceptable salts of compounds of formula (I). More particularly the present invention relates to the stable pharmaceutical composition of compounds of formula (I) comprising compounds of formula (I) or its pharmaceutically acceptable salts, wherein the pH of the formulation is maintained above 7. formula (I).

23 Claims, 1 Drawing Sheet

(56) References Cited

U.S. PATENT DOCUMENTS

| | | | |
|---|---|---|---|
| 5,273,995 | A | 12/1993 | Roth |
| 5,354,772 | A | 10/1994 | Kathawala |
| 6,166,063 | A | 12/2000 | Villhauer |
| 6,395,767 | B2 | 5/2002 | Robl et al. |
| 6,699,871 | B2 | 3/2004 | Edmondson et al. |
| 6,987,123 | B2 | 1/2006 | Lohray et al. |
| 7,041,837 | B2 | 5/2006 | Lohray et al. |
| 7,323,491 | B2 | 1/2008 | Lohray et al. |
| 7,407,955 | B2 | 8/2008 | Himmelsbach et al. |
| 8,110,598 | B2 | 2/2012 | Lohray et al. |
| 8,212,057 | B2 | 7/2012 | Lohray et al. |
| 8,558,009 | B2 | 10/2013 | Lohray et al. |
| 8,772,342 | B2 | 7/2014 | Darteil et al. |
| 9,610,277 | B2 | 4/2017 | Patel et al. |
| 9,656,954 | B2 | 5/2017 | Jain et al. |
| 2003/0199498 | A1 | 10/2003 | Lohray et al. |
| 2003/0236254 | A1 | 12/2003 | Lohray et al. |
| 2007/0238776 | A1 | 10/2007 | Lohray et al. |
| 2009/0196923 | A1 | 8/2009 | Mandal et al. |
| 2011/0275669 | A1 | 11/2011 | Lohray et al. |
| 2012/0121729 | A1 | 5/2012 | Paterson et al. |
| 2013/0338209 | A1 | 12/2013 | Gambhire et al. |
| 2016/0068484 | A1 | 3/2016 | Jain et al. |
| 2016/0107989 | A1 | 4/2016 | Dwivedi et al. |
| 2016/0136131 | A1 | 5/2016 | Patel et al. |
| 2016/0166539 | A1 | 6/2016 | Patel et al. |
| 2016/0194280 | A1 | 7/2016 | Dwivedi et al. |
| 2016/0207884 | A1 | 7/2016 | Dwivedi et al. |

FOREIGN PATENT DOCUMENTS

| | | |
|---|---|---|
| WO | WO-91/19702 A1 | 12/1991 |
| WO | WO-94/01420 A1 | 1/1994 |
| WO | WO-94/13650 A1 | 6/1994 |
| WO | WO-95/03038 A1 | 2/1995 |
| WO | WO-95/17394 A1 | 6/1995 |
| WO | WO-96/04260 A1 | 2/1996 |
| WO | WO-96/04261 A1 | 2/1996 |
| WO | WO-96/33998 A1 | 10/1996 |
| WO | WO-97/25042 A1 | 7/1997 |
| WO | WO-97/36579 A1 | 10/1997 |
| WO | WO-99/08501 A2 | 2/1999 |
| WO | WO-99/16758 A1 | 4/1999 |
| WO | WO-99/19313 A1 | 4/1999 |
| WO | WO-99/20614 A1 | 4/1999 |
| WO | WO-00/23417 A1 | 4/2000 |
| WO | WO-00/23445 A1 | 4/2000 |
| WO | WO-00/23451 A1 | 4/2000 |
| WO | WO-01/53257 A2 | 7/2001 |
| WO | WO-02/24625 A2 | 3/2002 |
| WO | WO-03/009841 A1 | 2/2003 |
| WO | WO-2005/031335 A1 | 4/2005 |
| WO | WO-2012/104869 A1 | 8/2012 |
| WO | WO-2014/174524 A1 | 10/2014 |
| WO | WO-2014/195967 A2 | 12/2014 |
| WO | WO-2015/001573 A1 | 1/2015 |
| WO | WO-2015/011730 A1 | 1/2015 |
| WO | WO-2015/029066 A1 | 3/2015 |
| WO | WO-2015/033357 A2 | 3/2015 |

OTHER PUBLICATIONS

Cairns, D. (editor) "Essentials of Pharmaceutical Chemistry, Fourth Edition" 2012, p. 14.

Bharate, S. et al. "Interactions and incompatibilities of pharmaceutical excipients with active pharmaceutical ingredients: a comprehensive review." *J. Excipient and Food Chem.* (2010) vol. 1, No. 3, pp. 3-26.

International Search Report and Written Opinion dated Nov. 20, 2014 for International Application No. PCT/IN2014/000489 (10 pages).

International Preliminary Report on Patentability dated Oct. 9, 2015 for International Application No. PCT/IN2014/000489 (7 pages).

Response to Written Opinion filed on May 21, 2015 for International Application No. PCT/IN2014/000489 (6 pages).

"Sodium Stearyl Fumarate", obtained on Jun. 23, 2015. Retrieved from the Internet: <URL: https://www.medicinescomplete.com/me/excipients/current/ . . . >, 4 pages.

International Search Report and Written Opinion dated Feb. 2, 2015 for International Patent Application No. PCT/IN2014/000367 (14 pages).

Jani, R. H. et al. "Pharmacokinetics, Safety, and Tolerability of Saroglitazar (ZYH1), a Predominantly PPARα Agonist with Moderate PPARγ Agonist Activity in Healthy Human Subjects" *Clin. Drug Investig.* (2013) vol. 33, pp. 809-816.

Brenna, E. et al. "Enzyme-mediated synthesis of EEHP and EMHP, useful pharmaceutical intermediates of PPAR agonists" *Tetrahedron: Asymmetry* (2009) vol. 20 pp. 2594-2599.

International Search Report and Written Opinion dated Mar. 23, 2015 for Application No. PCT/IN2014/000584 (14 pages).

International Search Report and Written Opinion dated Dec. 19, 2014 for Application No. PCT/IN2014/000551 (11 pages).

Demuth, H.-U. et al. "Type 2 diabetes—Therapy with dipeptidyl peptidase IV inhibitors," *Biochim. Biophys. Acta*, 1751 (2005) pp. 33-44.

Augustyns, K. et al. "Inhibitors of proline-specific dipeptidyl peptidases: DPP IV inhibitors as a novel approach for the treatment of Type 2 diabetes," *Expert Opin. Ther. Patents*, (2005) vol. 15, No. 10, pp. 1387-1407.

Pai, V. et al. "A Multicenter, Prospective, Randomized, Double-blind Study to Evaluate the Safety and Efficacy of Saroglitazar 2 and 4 mg Compared to Pioglitazone 45 mg in Diabetic Dyslipidemia (PRESS V)." *J. Diabetes Sci. Technol.* (2014) vol. 8, No. 1, pp. 132-141.

Jani, R. H. et al. "A Multicenter, Prospective, Randomized, Double-Blind Study to Evaluate the Safety and Efficacy of Saroglitazar 2 and 4 mg Compared with Placebo in Type 2 Diabetes Mellitus Patients Having Hypertriglyceridemia Not Controlled with Atorvastatin Therapy (PRESS VI)," Diabetes Technology & Therapeutics, (2014) vol. 16, No. 2, pp. 63-71.

International Search Report and Written Opinion dated Dec. 23, 2014 for International Patent Application No. PCT/IN2014/000445 (10 pages).

International Preliminary Report on Patentability dated Oct. 6, 2015 for International Patent Application No. PCT/IN2014/000445 (7 pages).

Lieberman, et al. "Pharmaceutical Dosage Forms: Tablets, vol. 1, 2nd Edition" (1989) Marcel Dekker Inc., pp. 111-114.

Gennaro et al. "Remington's Pharmaceutical Sciences, 19th Edition" (1995) Mack Publishing, pp. 1380-1383.

Anonymous International Nonproprietary Names for Pharmaceutical Substances (INN); Jan. 1, 2012; Retrieved from the Internet: URL: http://www.who.int/medicines/publications/druginformation/issues/PL_108.pdf; Retrieved on Oct. 15, 2013; pp. 401-471.

International Search Report and Written Opinion dated Nov. 20, 2013 for International Application No. PCT/IN2013/000391 (13 pages).

International Preliminary Report on Patentability dated Jul. 9, 2015 for International Application No. PCT/IN2013/000391 (9 pages).

IND Committee: "Minutes of IND Committee Meeting Held on Jul. 19, 2012" Retrieved on Oct. 15, 2013 from the Internet from URL: http://www.docstoc.com/docs/145152750/IND-Minutes-draft-19-07-12 (2 pages).

Anonymous "IND Minutes draft 19 07 12" Retrieved on Oct. 15, 2013 from the Internet from URL: http://www.docstoc.com/docs/145152750/IND-Minutes-draft-19-07-12 (1 page).

Anonymous "Lipaglyn™ Discovery, Development & Preclinical Studies" Retrieved on Oct. 15, 2013 from the Internet from URL: http://webcache.googleusercontent.com/search?q=cache:RGrhmY0HM3sJ:lipaglyn.com/downloads/Lipaglyn_Preclinical_Studies.ppsx (25 pages).

Jani, R. H. et al. "A Prospective Randomized, Double Blind, Placebo Controlled Study to Evaluate the Safety, Tolerability and Pharmacokinetics of ZYH1 Following Once a Day (OD) Oral Administrations up to 10 Days in Healthy Volunteers," *Diabetes* (2009) vol. 58, Suppl. 1, p. A569.

(56) References Cited

OTHER PUBLICATIONS

Ramirez, T. et al. "Structural Correlates of PPAR Agonist Rescue of Experimental Chronic Alcohol-Induced Steatohepatitis," *J. Clin. Exper. Pathology* (2012) vol. 2, No. 4, pp. 1-9.
Seo, Y. S. et al. "PPAR agonists treatment is effective in a nonalcoholic fatty liver disease animal model by modulating fatty-acid metabolic enzymes" *J. Gatroenterology Hepatology* (2008) vol. 23, No. 1, pp. 102-109.
Barb et al. (2016) "Pharmacological management of nonalcoholic fatty liver disease" Metabolism Clinical and Experimental 65:1183-1195.
Berger et al. (2005) "PPARs: Therapeutic targets for metabolic disease" Trends in Pharmacological Sciences 26(5): 244-251.
Chou et al. (2013) "Metrelepin: First Global Approval" Drugs 73:989-997.
Deeg et al. (2007) "Pioglitazone and Rosiglitazone Have Different Effects on Serum Lipoprotein Particle Concentrations and Sizes in Patients With Type 2 Diabetes and Dyslipidemia" Diabetes Care 30(10):2458-2464.
FDA News Release—FDA Approves Egrifta to treat Lipodystrophy in HIV Patients; downloaded from www.fda.gov/NewsEvents/Newsroom/PressAnnouncements/ucm233516.htm on Sep. 7, 2016 (2 pages).
Giri et al. "Efficacy of Saroglitazar, a Novel PPAR Agonist in a Mouse Model of Non-Alcoholic Steatohepatitis" Poster No. 2011, Keystone Symposia Conference, Mar. 22-27, 2015 at Whistler, British Colombia, Canada.
Jain et al. "Saroglitazar Shows Therapeutic Benefits in Mouse Model of Non-alcoholic Fatty Liver Disease (NAFLD) and Non-alcoholic Steatohepatitis (NASH)" Poster No. 1957-P, 75th Scientific Session—ADA, Jun. 5-9, 2015, Boston, MA, USA.
Package Insert for ACTOS (pioglitazone) tablets for oral use (2013).
Package Insert for AVANDIA (rosiglitazone maleate) Tablets (2008).
Palomer et al. (2016) "PPARβ/δ and lipid metabolism in the heart" Biochemica et Biophysics Acta 1861:1569-1578.
Yessoufou et al. (2010) "Multifaceted roles of peroxisome proliferator-activated receptors (PPARs) at the cellular and whole organism levels" Swiss Medical Weekly 140:w13071.
International Search Report dated May 9, 2012 for International Application No. PCT/IN2012/000069 (3 pages).
van Wijk, J. P. H. et al. "Comparison of Rosiglitazone and Metformin for Treating HIV Lipodystrophy: A Randomized Trial," *Ann. Internal Med.* (2005) vol. 143, No. 5, pp. 337-346.
Hadigan, C. et al. "Metabolic Effects of Rosiglitazone in HIV Lipodystrophy: A Randomized, Controlled Trial," *Ann. Internal Med.* (2004) vol. 140, No. 10, pp. 788-794. (Abstract Only).
Macallan, D. C. etal. "Treatment of Altered Body Composition in HIV Associated Lipodystrophy: Comparison of Rosiglitazone, Pravastatin, and Recombinant Human Growth Hormone," *HIV Clinical Trials*, (2008) vol. 9, Issue 4, pp. 254-268. (Abstract Only).
Tungsiripat, M. et al. "Rosiglitazone improves lipoatrophy in patients receiving thymidine-sparing regimens," *AIDS*, (2010) vol. 24, pp. 1291-1298.
Fan, W. and Evans, R. "PPARs and ERRs: molecular mediators of mitochondrial metabolism" *Curr. Opin. Cell Bio.* (2015) vol. 33, pp. 49-54.
LaBrecque, D. et al. "World Gastroenterology Organisation, Global Guidelines: Nonalcoholic Fatty Liver disease and Nonalcoholic Steatohepatitis (long version)" World Gastroenterology Organisation (2012) 29 pages.
International Preliminary Report on Patentability dated Aug. 15, 2013 for International Application No. PCT/IN2012/000069 (5 pages).
International Preliminary Report on Patentability dated Dec. 1, 2015 for International Patent Application No. PCT/IN2014/000367 (9 pages).
International Preliminary Report on Patentability dated Mar. 1, 2016 for Application No. PCT/IN2014/000551 (7 pages).
International Preliminary Report on Patentability dated Mar. 8, 2016 for International Patent Application No. PCT/IN2014/000584 (10 pages).
Written Opinion of the International Searching Authority dated May 9, 2012 for International Application No. PCT/IN2012/000069 (4 pages).
Pharmatrans Sanaq AG "LubriSanaq" Dated Feb. 5, 2008. (2 pages).
Lemoine, M. et al. "Steatohepatitis (fatty liver) Is Associated With Increased Hepatic Expression of SREBP-1 in HIV-Infected Patients With Antiretroviral Therapy-Linked Lipodystrophy," Abstract from 55th Annual Meeting of the American Association for the Study of Liver Diseases, Oct. 29-Nov 2, 2004; Printed from http://www.natap.org/2004/AASLD/aasld_10.htm. (8 pages).
Bugianesi, E. et al. "Insulin Resistance: A Metabolic Pathway to Chronic Liver Disease," *Hepatology* (2005) vol. 42, No. 5, pp. 987-1000.
Angulo, P. "GI Epidemiology: nonalcoholic fatty liver disease," *Aliment. Pharmacol. Ther.* (2007) vol. 25, No. 8, pp. 883-889.
Acdisol Product Overview (year 2005).
USPTO Trademark Database Entry for AEROSIL.
U.S. Appl. No. 13/978,791, filed Sep. 4, 2013, Treatment for Lipodystrophy.
U.S. Appl. No. 15/345,035, filed Nov. 7, 2016, Treatment for Lipodystrophy.
U.S. Appl. No. 15/343,859, filed Nov. 4, 2016, Novel Composition for Nonalcoholic Fatty Liver Disease (NAFLD).
U.S. Appl. No. 15/594,795, filed May 15, 2017, Synergistic Compositions.
U.S. Appl. No. 14/916,402, filed Mar. 3, 2016, Improved Process for the Preparation of Pyrrole Derivatives.
U.S. Appl. No. 14/894,744, filed Nov. 30, 2015, A Process for Preparation of Pyrroles Having Hypolipidemic Hypocholesteremic Activities.
U.S. Appl. No. 15/366,229, filed Dec. 1, 2016, A Process for Preparation of Pyrroles Having Hypolipidemic Hypocholesteremic Activities.
U.S. Appl. No. 14/915,457, filed Feb. 29, 2016, Polymorphic Form of Pyrrole Derivative and Intermediate Thereof.

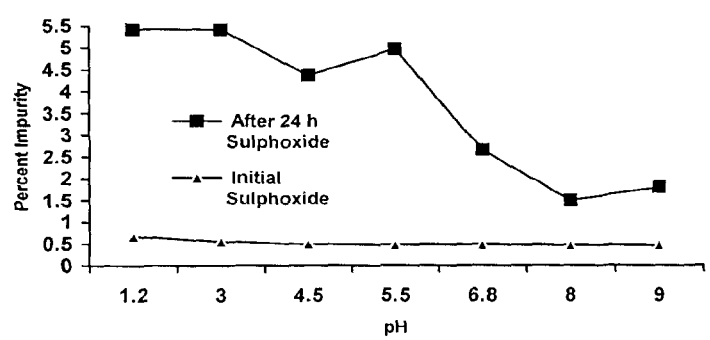

FORMULA COMPRISING A HYPOLIPIDEMIC AGENT

CROSS-REFERENCE TO RELATED APPLICATIONS

This application is a continuation of U.S. patent application Ser. No. 14/899,912, filed Dec. 18, 2015, which is the national stage of International (PCT) Patent Application Serial No. PCT/IN2014/000489, filed Jul. 24, 2014, which claims the benefit of and priority to Indian Patent Application No. 2470/MUM/2013, filed Jul. 25, 2013; the contents of International Patent Application Serial No. PCT/IN2014/000489 and U.S. patent application Ser. No. 14/899,912 are hereby incorporated by reference in their entirety.

FIELD OF THE INVENTION

The present invention relates to stable pharmaceutical compositions of a suitable hypolipidemic agent. Preferably, the present invention discloses novel formulations of the compound of formula (I), or pharmaceutically acceptable salts of compounds of formula (I). More particularly the present invention relates to the stable pharmaceutical composition of compounds of formula (I) comprising compounds of formula (I) or its pharmaceutically acceptable salts, wherein the pH of the formulation is maintained above 7.

BACKGROUND OF THE INVENTION

The compounds of formula (I) are new synthetic compounds having hypolipidemic activity. The compounds of formula (I) are used primarily for triglyceride lowering, with concomitant beneficial effect on glucose lowering and cholesterol lowering.

The structural formula of compounds of formula (I) is shown below.

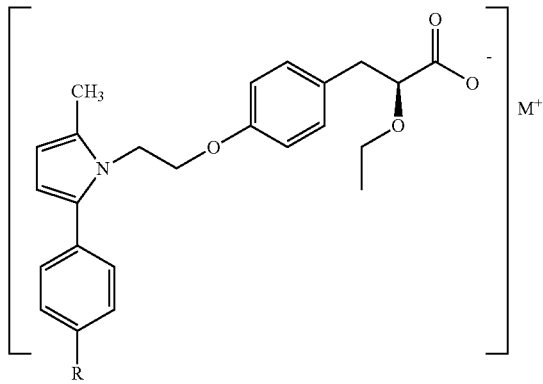

wherein 'R' is selected from hydroxy, hydroxyalkyl, acyl, alkoxy, alkylthio, thioalkyl, aryloxy, arylthio and represents suitable metal cations such as $Na^+$, $K^+$, $Ca^{+2}$, $Mg^{+2}$ and the like. Preferably, R is selected from alkylthio or thioalkyl groups; most preferably R represents $-SCH_3$. The $Mg^{+2}$ salt is preferred. The compounds of formula (I) are generally insoluble in water, but freely soluble in dimethyl sulfoxide, dichloromethane & slightly soluble in methanol and IPA.

The compounds of formula (I) are susceptible to oxidation, alkaline & acid hydrolysis and stress degradation during synthesis, purification and storage of the drug substance or when formulated as a dosage form. Sulfoxide and sulfone derivatives are the potential oxidized product.

The handling and storage particularly in the bulk form of pharmaceutically active ingredients which are sensitive to oxidation is difficult. Special handling is necessary and often the oxidation-sensitive ingredients are stored in airtight packaging under protective gas. Substantial amounts of stabilizers are added during the formulating process of such pharmaceutically active ingredients. In order to have a stable composition of compounds of formula (I), which meets the regulatory requirements, therefore, special packaging conditions will be required which is costly, difficult to manage and difficult to use in an industrial scale. Therefore, it is necessary to develop an alternate formulation which can stabilize the compound of formula (I) such that the expensive packaging requirements can be overcome.

The inventors of the present invention surprisingly found that when suitable alkalinizer(s) are added into the formulation, the formulation remains stable. Further, one of the impurity (sulfoxide) which was being generated in API increases from 0.17% to 0.76% over a period of 6 months. Surprisingly, when suitable alkalinizer(s) are added which maintains the pH of the formulation above 7, the increase in the level of said impurity is restricted (from 0.13% to 0.26% over six months with no further increase with time). Therefore stabilization of compositions containing compounds of formula (I) can be made by maintaining the microenvironmental pH of composition above 7 by using suitable alkalinizers. Use of a suitable antioxidant(s) and chelating agent(s) further stabilizes the formulation.

SUMMARY OF THE INVENTION

The present invention, describes a stable pharmaceutical composition of compounds of formula (I) or their derivatives, wherein the microenvironmental pH of the composition is maintained above 7.

DESCRIPTION OF FIGURES

FIG. 1: Percentage of sulfoxide impurity level (0.3 RRT) at different pH after 24 hours.

FIG. 1 shows the percentage impurity level of sulfoxide. When the pH was modulated by addition of alkalinizer(s) then sulfoxide impurity level in API is restricted.

DETAILED DESCRIPTION OF THE INVENTION

The present invention describes a stable pharmaceutical composition of compounds of formula (I) or their derivatives,

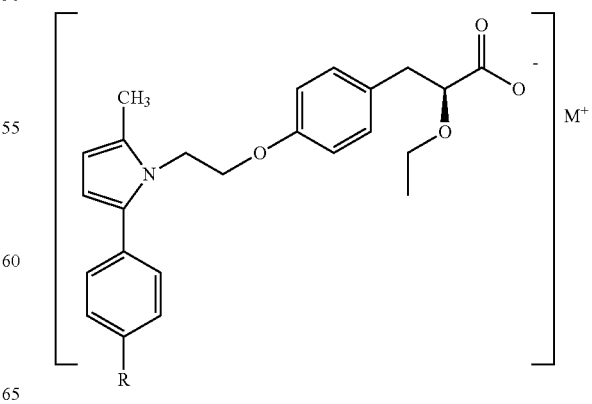

wherein 'R' is selected from hydroxy, hydroxyalkyl, acyl, alkoxy, alkylthio, thioalkyl, aryloxy, arylthio and $M^+$ represents suitable metal cations such as Na+, K+, Ca+2, Mg+2 and the like and wherein the pH of the composition is maintained above 7.

In a preferred embodiment the compound of formula (I) represents Saroglitazar Magnesium of formula (Ia) having the chemical name Benzenepropanoic acid, α-ethoxy-4-[2-[2-methyl-5-[4-(methylthio)phenyl]-1H-pyrrol-1-yl] ethoxy] magnesium salt and having the following structure

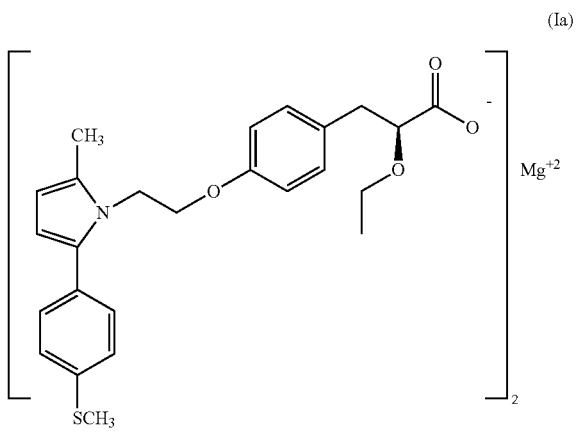

(Ia)

The present invention further describes a stable pharmaceutical composition of compounds of formula (I) or their derivatives, preferably a compound of formula (Ia), comprising one or more pharmaceutical excipients, alkalinizers, antioxidants and chelating agents, wherein the pH of the composition is maintained above 7.

The pharmaceutical composition of compound of formula (I) or their derivatives of the present invention essentially comprises of
suitable alkalinizers or suitable pH modifying agents which maintain the pH of the formulation above 7, and optionally
a suitable stabilizer (antioxidants and chelating agents); and one or more other pharmaceutically acceptable excepients.

Suitable stabilizers may be selected from the classes of antioxidants or chelating agents. The other pharmaceutical excepients according to the present invention can be selected from suitable diluents, fillers, disintegrants, binder, lubricants, glidants, wetting agents, solvents and the like as is known in the art.

Antioxidants used according to the present invention include, but are not limited to citric acid, alpha tocopherol, sodium sulphite, sodium metabisulphite, butylated hydroxy anisole (BHA), BHT (2,6-di-tert-butyl-4-methylphenol), monothioglycerol, Vitamin C (ascorbic acid), and propyl gallate and combinations thereof and other similar material known to those of the ordinary skilled in the art.

Chelating agent used according to the present invention include, but are not limited to Disodium EDTA, citric acid and or its salts, maleic acid, chlorambutol, chlorhexidine or its salts, chlorocresol, combinations thereof and other similar material known to those of ordinary skill in the art.

Alkalinizers or suitable pH modifying agents which maintain the pH of the formulation above 7 used according to the present invention include, but are not limited to attapulgite, bentonite, calcium carbonate, calcium phosphate, calcium sulphate, mono ethanolamine, tri ethanolamine, potassium bicarbonate, potassium citrate, potassium hydroxide, sodium benzoate, sodium hydroxide, sodium sulfite, sodium bicarbonate, sodium carbonate, Disodium Hydrogen phosphate, mono basic potassium phosphate, Dicalcium phosphate, meglumine, light or heavy magnesium oxide and other similar excipients and their suitable combinations and other materials known to those of ordinary skill in the art.

As used herein, the term "binders" is intended to mean substances used to cause adhesion of powder particles in tablet granulations. Such compounds include, by way of example and without limitation, acacia alginic acid, tragacanth, carboxymethylcellulose sodium, poly (vinylpyrrolidone), compressible sugar (e.g., NuTab), ethyl cellulose, gelatin, liquid glucose, methyl cellulose, povidone and pregelatinized starch, combinations thereof and other similar materials known to those of ordinary skill in the art.

When needed, other binders may also be included in the present invention. Exemplary binders include starch, poly (ethylene glycol), guar gum, polysaccharide, bentonites, sugars, invert sugars, poloxamers (PLURONIC F68, PLURONIC F127), collagen, albumin, celluloses in non-aqueous solvents, and the like or their suitable combinations. Other binders which may be included may be, for example, poly(propylene glycol), polyoxyethylene-polypropylene copolymer, polyethylene ester, polyethylene sorbitan ester, poly(ethylene oxide), microcrystalline cellulose, poly(vinylpyrrolidone), combinations thereof and other such materials known to those of ordinary skill in the art.

As used herein, the term "diluent" or "filler" is intended to mean inert substances used as fillers to create the desired bulk, flow properties, and compression characteristics in the preparation of tablets and capsules. Such compounds include, by way of example and without limitation, dibasic calcium phosphate, kaolin, sucrose, mannitol, microcrystalline cellulose, powdered cellulose, precipitated calcium carbonate, sorbitol, starch, combinations thereof and other such materials known to those of ordinary skill in the art.

As used herein, the term "glidant" is intended to mean agents used in tablet and capsule formulations to improve flow-properties during tablet compression and to produce an anti-caking effect. Such compounds include, by way of example and without limitation, colloidal silica, calcium silicate, magnesium silicate, silicon hydrogel, cornstarch, talc, combinations thereof and other such materials known to those of ordinary skill in the art.

As used herein, the term "lubricant" is intended to mean substances used in tablet formulations to reduce friction during tablet compression. Such compounds include, by way of example and without limitation, calcium stearate, magnesium stearate, mineral oil, stearic acid, zinc stearate, suitable combinations thereof and other such materials known to those of ordinary skill in the art.

As used herein, the term "disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pregelatinized and modified starched thereof, sweeteners, clays, such as bentonite, microcrystalline cellulose (e.g. Avicel™), carsium (e.g. Amberlite™), alginates, sodium starch glycolate, gums such as agar, guar, locust bean, karaya, pectin, tragacanth, combinations thereof and other such materials known to those of ordinary skill in the art.

As used herein, the term "wetting agent" is intended to mean a compound used to aid in attaining intimate contact between solid particles and liquids. Exemplary wetting agents include, by way of example and without limitation, poloxamers, gelatin, casein, Glycerol mono-oleate, lecithin (phosphatides), gum acacia, cholesterol, tragacanth, stearic acid, benzalkonium chloride, calcium stearate, glycerol monostearate, cetostearyl alcohol, sodium lauryl sulphate, sodium dodecyl sulfate, salts of bile acids (taurocholate, glycocholate, cholate, deoxycholate, etc.), cetomacrogol emulsifying wax, sorbitan esters, polyoxyethylene alkyl ethers (e.g., macrogol ethers such as cetomacrogol 1000), polyoxyethylene castor oil derivatives, polyoxyethylene sorbitan fatty acid esters, (e.g., TWEEN), polyethylene glycols, polyoxyethylene stearates colloidal silicon dioxide, phosphates, sodium dodecylsulfate, carboxymethylcellulose calcium, carboxy methylcellulose sodium, methyl cellulose, hydroxyethylcellulose, hydroxylpropylcellulose, hydroxy propyl methyl cellulose phthalate, noncrystalline cellulose, magnesium aluminum silicate, triethanolamine, polyvinyl alcohol, and poly vinyl pyrrolidone (PVP) & their suitable combinations and other such materials known to those of ordinary skill in the art. Tyloxapol (a nonionic liquid polymer of the alkyl aryl polyether alcohol type, also known as superinone or triton) is another useful wetting agent which may be used.

The stable pharmaceutical composition according to the present invention may be in the form of a tablet or a caplet or a capsule or a powder or a suspension in a liquid or an aerosol formulation or solutions, preferably in the form of a tablet or capsule.

In another embodiment of the present invention, is described processes for the preparation of a stable pharmaceutical composition of compounds of formula (I), preferably a compound of formula (Ia), or their derivatives.

The stable pharmaceutical composition may be made by direct compression, wet granulation or dry granulation methods by techniques known to persons skilled in the art. Thus, for example, in the wet granulation process, the drug is mixed with one or more pharmaceutical excepients and granulated with suitable binding solution to form wet granules, the wet granules are dried and optionally sieved. The dried granules are mixed with one or more suitable excepients from those described elsewhere and then compressed into tablets or filled into capsules.

In direct compression process, the drug is mixed with all the pharmaceutical excepients required and then is either compressed into tablets or filled in capsules.

In dry granulation process, the drug is mixed with one or more pharmaceutical excepients and compressed into slugs and these slugs are passed through required sieve. The sieved granules are mixed with one or more suitable excepients from those described elsewhere and then compressed into tablets or filled into capsules.

One or more solvents used in the formulation are selected from acetone, chloroform, dichloromethane, ethyl alcohol, ethyl acetate, methyl alcohol, isopropyl alcohol and combinations thereof and other such materials known to those of ordinary skill in the art.

About 1% w/v aqueous dispersion of tablets was used for pH measurement. pH degradation can be seen with API when kept in different standard pH buffers. Percentage individual impurity at 0.3 RRT (Sulphoxide impurity) decreases as the solution of pH increases above pH 7 as shown in FIG. 1.

The invention as described earlier is further demonstrated in illustrative examples 1 to 9 below. These examples are provided as illustration only and therefore should not be considered as a limitation of the scope of the invention.

The following formulations were prepared using different chelating agents, alkalinizers and anti-oxidants by dry granulation techniques:

Brief Manufacturing Procedure:

1.0. Granulation i) Intragranular excipients and API [compound of formula (IA)] are weighed accurately and mixed properly.

ii) To the dry blend IPA is added and the blend is granulated.

iii) Wet mass is passed through #10 and the wet granules are dried in FBD at a temperature below 60° C.

Extragranular Addition

Colloidal silicon is weighed and passed along with the dried granules through #30. The colloidal silicon is mixed with the granules in the conta blender and to the dried mass Talc and Magnesium stereate is added and mixed.

2.0. Direct Compression

All intragranular excipients and API are weighed accurately and mixed properly and blended in the conta blender. Extragranular excipients were added and lubricated in conta blender. The granules or blend is compressed into tablets or filled into capsules.

3.0 Dry Granulation

All excipients are mixed and passed through a roller compactor. Obtained pellets are then subjected to milling to get uniform powder which is the lubricated and followed by compression.

TABLE 1

| Test | Percent Purity at 40° C./75% RH | | | |
| --- | --- | --- | --- | --- |
| | Initial | 1 Month | 2 Month | 3 Month |
| Purity | 98.48 | 98.10 | 97.93 | 97.17 |
| Water By KF | 0.62 | 1.17 | 2.32 | 2.57 |

Table 1 shows that moisture absorption of API increases when exposed to 40° C./75% RH condition. Therefore the inventors of the present invention have tried to develop a stable formulation of API such that the API is protected and cannot absorb moisture.

Initial formulations without alkalinizers were prepared as provided in Table 2 and were tested for their stability by loading them in stability chambers as per techniques and protocols known in the art as shown in Table 2. Table 3 provides the stability data of these formulations.

TABLE 2

| | % w/w | | |
| --- | --- | --- | --- |
| Ingredient | Ex 1 | Ex 2 | Ex 3 |
| Compound (Ia) | 1.00 | 1.54 | 1.54 |
| Disodium EDTA | 2.00 | — | — |
| Disodium hydrogen phosphate | — | — | — |
| Light magnesium oxide | — | — | — |
| Meglumin | — | — | — |
| Sodium Bicarbonate | — | — | — |
| Sodium metabisulfite | — | 1.00 | 0.50 |
| Propyl Gallate | — | — | — |
| Alpha Tocopherol | 8.00 | — | — |
| Lactose Anhydrous | — | 86.81 | 87.31 |
| Microcrystalline cellulose | — | — | — |

TABLE 2-continued

| | % w/w | | |
|---|---|---|---|
| Ingredient | Ex 1 | Ex 2 | Ex 3 |
| Dibasic Calcium Phosphate | 65.50 | — | — |
| Acdisol | 14.00 | 4.15 | 4.15 |
| Povidone K-30 | 6.00 | 5.00 | 5.00 |
| Purified water | — | — | — |
| Puririfed Talc | 1.00 | 0.50 | 0.50 |
| Aerosil | 1.50 | 0.50 | 0.50 |
| Magnesium Stearate | 1.00 | 0.50 | 0.50 |

TABLE 3

One month stability data of the formulations of Table 2

| | Percent Purity at 40° C./75% RH | |
|---|---|---|
| Batch No. | Initial | 1 Month |
| Ex 1 | 97.89 | 91.57 |
| Ex 2 | 98.58 | 96.88 |
| Ex 3 | 98.59 | 97.39 |

It can be seen that from Table 3 that these formulations which do not contain any alkalinizers have poor stability.

Subsequently, alkalinizers were added and table 4 shows such alkalizer containing formulations. These formulations were also tested for their stability by loading them in stability chambers as per techniques and protocols known in the art as shown in Table 5.

TABLE 4

| Ingredient | Ex 4 | Ex 5 | Ex 6 | Ex 7 | Ex 8 | Ex 9 |
|---|---|---|---|---|---|---|
| Compound (Ia) | 3.08 | 1.54 | 1.54 | 1.54 | 1.54 | 1.54 |
| Disodium EDTA | — | — | — | — | — | 2.00 |
| Disodium hydrogen phosphate | — | — | 1.00 | 1.00 | 1.00 | 1.00 |
| Light magnesium oxide | 6.15 | — | — | — | — | — |
| Meglumin | — | — | — | — | — | — |
| Sodium Bicarbonate | — | 9.00 | — | — | — | — |
| Sodium metabisulfite | — | — | 1.00 | — | — | — |
| Propyl Gallate | — | — | — | 0.10 | — | — |
| Alpha Tocopherol | — | — | — | — | 8.00 | — |
| Lactose Anhydrous | 23.07 | 78.81 | 85.81 | 86.71 | 78.81 | 84.81 |
| Microcrystalline cellulose | 50.00 | — | — | — | — | — |
| Dibasic Calcium Phosphate | — | — | — | — | — | — |
| Acdisol | 9.23 | 4.15 | 4.15 | 4.15 | 4.15 | 4.15 |
| Povidone K-30 | 3.85 | 5.00 | 5.00 | 5.00 | 5.00 | 5.00 |
| Purified water | — | — | — | — | — | — |
| Puririfed Talc | 1.54 | 0.50 | 0.50 | 0.50 | 0.50 | 0.50 |
| Aerosil | 1.54 | 0.50 | 0.50 | 0.50 | 0.50 | 0.50 |
| Magnesium Stearate | 1.54 | 0.50 | 0.50 | 0.50 | 0.50 | 0.50 |

TABLE 5

Three months stability data of the formulations of Table 4

| Ex No | Initial | 1 Month | 2 Month | 3 Month |
|---|---|---|---|---|
| Ex 4 | 99.10 | 98.60 | 98.50 | 98.30 |
| Ex 5 | 98.40 | 98.03 | 97.66 | 97.53 |
| Ex 6 | 98.43 | 98.17 | 97.5 | 97.45 |
| Ex 7 | 98.36 | 97.82 | 97.6 | 97.44 |
| Ex 8 | 98.46 | 98.06 | 97.83 | 97.42 |
| Ex 9 | 98.34 | 97.78 | 97.52 | 97.42 |

The formulations containing alkalinizer are stable as can be seen from the above table 5.

The above stability data shows that the formulations are stable and the compound of formula (I) is effectively stabilized by addition of suitable alkalinizers so that it may be used in clinical trials and subsequently as a commercial product.

We claim:

1. A stable pharmaceutical composition comprising a compound of formula (Ia):

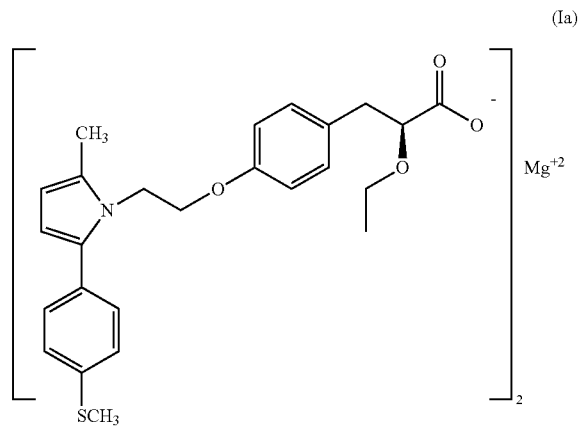

wherein:
the pH of the composition is above 7, and the composition comprises
an alkalinizer or pH modifying agent which maintains the pH of the pharmaceutical composition above 7, wherein the alkalinizer or pH modifying agent is light or heavy magnesium oxide; and
optionally a stabilizer and one or more other pharmaceutically acceptable excipients.

2. The pharmaceutical composition of claim 1, wherein the pharmaceutical composition comprises a binder.

3. The pharmaceutical composition of claim 1, wherein the pharmaceutical composition comprises microcrystalline cellulose.

4. The pharmaceutical composition of claim 1, wherein the pharmaceutical composition comprises povidone.

5. The pharmaceutical composition of claim 3, wherein the pharmaceutical composition comprises povidone.

6. The pharmaceutical composition of claim 1, wherein the pharmaceutical composition comprises a glidant.

7. The pharmaceutical composition of claim 2, wherein the pharmaceutical composition comprises a glidant.

8. The pharmaceutical composition of claim 1, wherein the pharmaceutical composition comprises talc.

9. The pharmaceutical composition of claim 4, wherein the pharmaceutical composition comprises talc.

10. The pharmaceutical composition of claim 5, wherein the pharmaceutical composition comprises talc.

11. The pharmaceutical composition of claim 1, wherein the pharmaceutical composition comprises a lubricant.

12. The pharmaceutical composition of claim 7, wherein the pharmaceutical composition comprises a lubricant.

13. The pharmaceutical composition of claim 1, wherein the pharmaceutical composition comprises magnesium stearate.

14. The pharmaceutical composition of claim 5, wherein the pharmaceutical composition comprises magnesium stearate.

15. The pharmaceutical composition of claim 10, wherein the pharmaceutical composition comprises magnesium stearate.

16. The pharmaceutical composition of claim 1, wherein the alkalinizer or pH modifying agent is light magnesium oxide.

17. The pharmaceutical composition of claim 5, wherein the alkalinizer or pH modifying agent is light magnesium oxide.

18. The pharmaceutical composition of claim 15, wherein the alkalinizer or pH modifying agent is light magnesium oxide.

19. The pharmaceutical composition of claim 1, wherein the pharmaceutical composition comprises:
3.08% w/w compound of formula Ia;
6.15% w/w light magnesium oxide;
23.07% w/w lactose anhydrous;
50.00% w/w microcrystalline cellulose;
9.23% w/w croscarmellose sodium;
3.85% w/w povidone K-30;
1.54% w/w purified talc;
1.54% w/w colloidal silicon dioxide; and
1.54% w/w magnesium stearate.

20. A tablet or caplet, comprising a pharmaceutical composition of claim 1.

21. A tablet or caplet, comprising a pharmaceutical composition of claim 5.

22. A tablet or caplet, comprising a pharmaceutical composition of claim 18.

23. A tablet or caplet, comprising a pharmaceutical composition of claim 19.

* * * * *